United States Patent
Clawson et al.

(10) Patent No.: US 6,436,714 B1
(45) Date of Patent: Aug. 20, 2002

(54) SELF-CONTAINED SYSTEM AND METHOD FOR TESTING FOR FECAL OCCULT BLOOD

(75) Inventors: Burrell E. Clawson, Newport Beach, CA (US); Steven B. Moss, Warwick, RI (US)

(73) Assignee: Diagnostica, Inc., Las Vegas, NV (US)

( * ) Notice: Subject to any disclaimer, the term of this patent is extended or adjusted under 35 U.S.C. 154(b) by 0 days.

(21) Appl. No.: 09/132,439

(22) Filed: Aug. 11, 1998

(51) Int. Cl.[7] ................................................ G01N 33/49
(52) U.S. Cl. ............................ 436/66; 422/61; 422/58; 436/166; 436/169
(58) Field of Search ........................ 422/56, 58, 61; 436/164, 166, 169, 811, 66

(56) References Cited

U.S. PATENT DOCUMENTS

| | | |
|---|---|---|
| 4,071,317 A | 1/1978 | Lam |
| 4,333,734 A | 6/1982 | Fleisher |
| 4,365,970 A | 12/1982 | Lawrence et al. |
| 4,382,064 A | 5/1983 | Detweiler et al. |
| D281,903 S | 12/1985 | Duffy |
| 4,562,043 A * | 12/1985 | Mennen et al. ............... 422/56 |
| 4,582,685 A * | 4/1986 | Guadagno et al. ............ 422/61 |
| 4,615,982 A | 10/1986 | Lawrence |
| 4,645,743 A | 2/1987 | Baker et al. |
| 4,738,823 A * | 4/1988 | Engelmann .................. 422/58 |
| 4,789,629 A | 12/1988 | Baker et al. |
| 4,818,702 A | 4/1989 | Lawrence |
| 4,937,197 A | 6/1990 | Lawrence |
| 4,939,097 A | 7/1990 | Lawrence |
| 4,983,416 A | 1/1991 | Hunsinger et al. |
| 5,100,619 A | 3/1992 | Baker et al. |
| 5,106,582 A | 4/1992 | Baker et al. |
| 5,137,808 A * | 8/1992 | Ullman et al. ................ 435/7.9 |
| 5,171,529 A | 12/1992 | Schreiber |
| 5,182,191 A | 1/1993 | Fan et al. |
| 5,196,167 A * | 3/1993 | Guadagno et al. ............ 422/56 |
| 5,198,365 A | 3/1993 | Grow et al. |
| 5,217,874 A | 6/1993 | Guadagno et al. |
| 5,264,181 A | 11/1993 | Schreiber |
| 5,310,680 A | 5/1994 | Baker et al. |
| 5,344,762 A | 9/1994 | Karapetian |
| 5,391,498 A | 2/1995 | Baker et al. |
| 5,504,013 A * | 4/1996 | Senior ........................ 436/165 |
| 5,840,584 A * | 11/1998 | Waldenburg .................. 436/66 |
| 6,077,711 A * | 6/2000 | Singer ......................... 422/58 |

\* cited by examiner

Primary Examiner—Lyle A. Alexander
(74) Attorney, Agent, or Firm—Stout, Uxa, Buyan & Mullins, LLP; Frank J. Uxa

(57) ABSTRACT

Self-contained systems test for the presence of occult blood in a specimen. In one embodiment, the system has a test matrix comprising a testing portion spaced apart from a medium entrance portion, wherein the testing portion has a specimen placement area on a first side and a result area on an opposing second side. The system also has a container holding a developing medium, wherein the container is adapted to release the developing solution onto the solution entrance portion. A housing holds the test matrix and the container. The housing has a specimen opening at the specimen placement area and preferably is adapted to enable the result area to be observed. The developing medium preferably is a free standing liquid within the container. The developing medium is released from the container upon compression or breaking of the container.

24 Claims, 3 Drawing Sheets

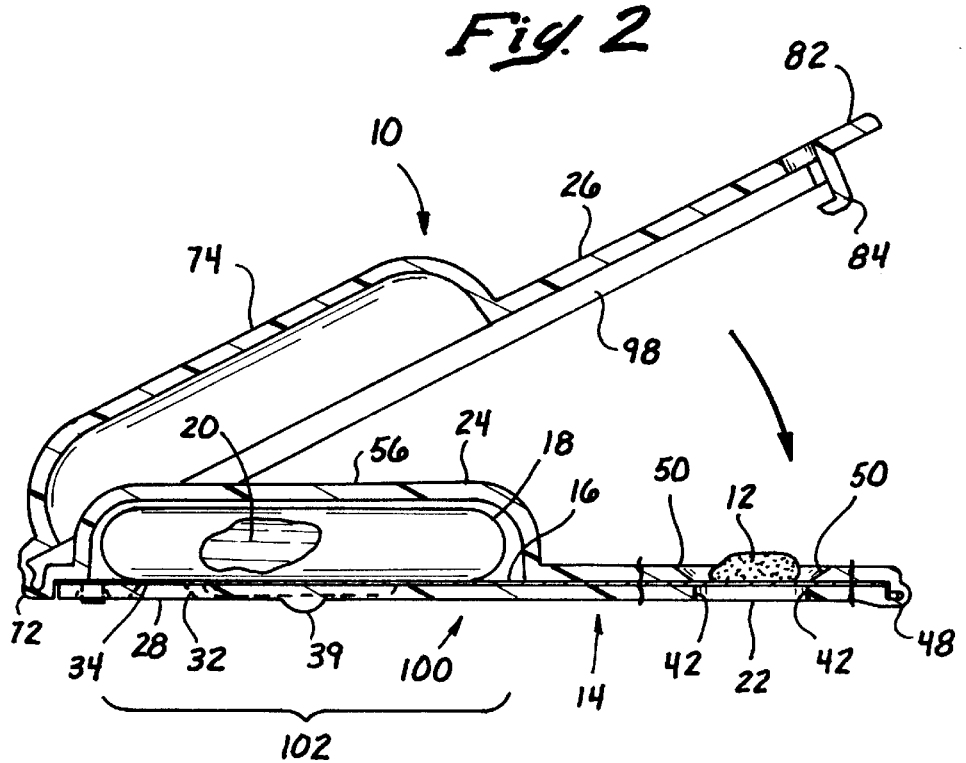
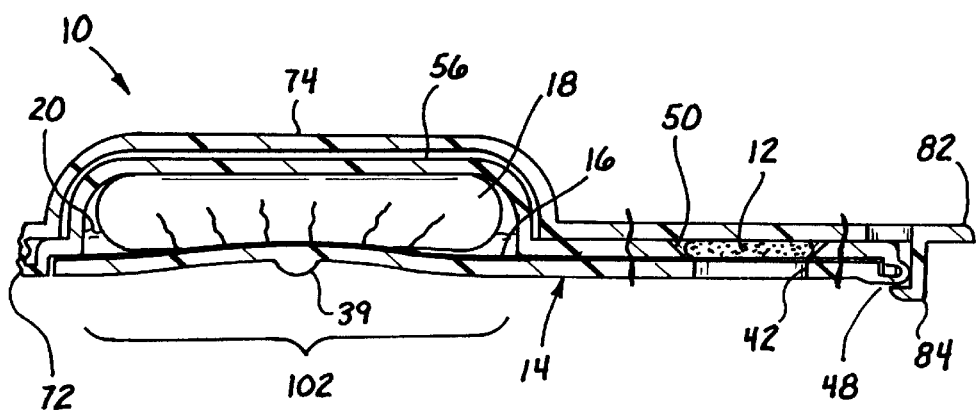

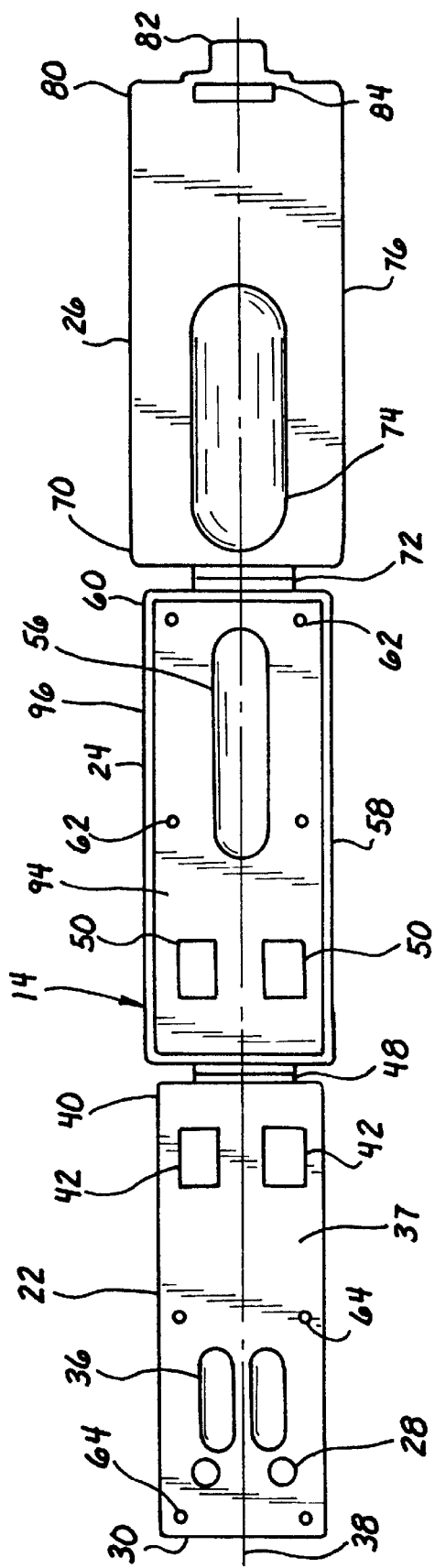
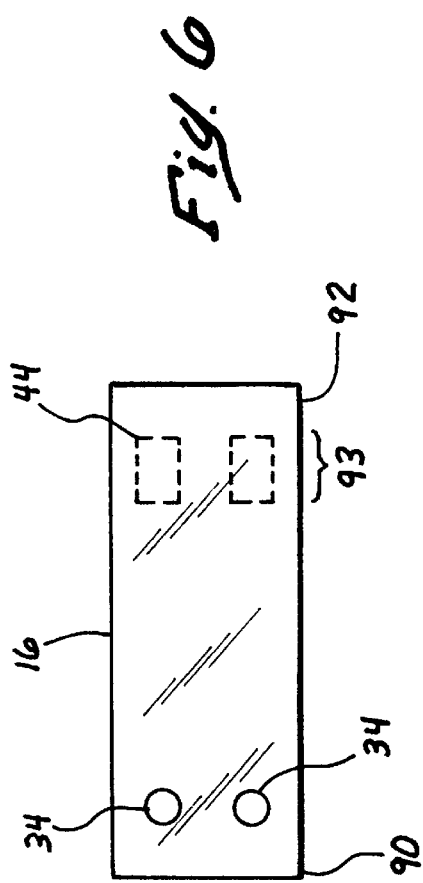
Fig. 3
Fig. 6

SELF-CONTAINED SYSTEM AND METHOD FOR TESTING FOR FECAL OCCULT BLOOD

BACKGROUND OF THE INVENTION

The present invention is directed to systems and methods useful in testing for occult blood in a specimen. More particularly, the invention is directed to such systems and methods that are convenient and safe to use and provide accurate results.

Over 100,000 persons per year in the United States are afflicted with cancer of the colon and rectum, the disease, occurring equally in both men and women. When the number of colon/rectal cancers occurring each year is combined with the number of cancers occurring in other digestive organs, including the esophagus and stomach, such cancers of the digestive system account for more occurrences of cancer than any other single form of the disease. Contrary to many other forms of cancer, early diagnosis and treatment of digestive tract cancer does result in a cure rate of 80% to 90%. If, however, the disease is not detected until the later stages, the cure rate drops significantly. Thus, early detection of the disease is important to successful treatment of digestive tract cancer.

Most, but not all, cancers of the digestive tract bleed to a certain extent. This blood is deposited on and in fecal matter excreted from the digestive system. The presence of blood in fecal matter is not normally detected, however, until gross bleeding, that is, blood visible to the naked eye, occurs. Most advance cancers of this type cause gross bleeding.

It is known that digestive tract cancers in the early stages tend to bleed, giving rise to occult (hidden) blood in the fecal matter. Test equipment and test procedures have been developed for use by physicians in testing for the presence of occult blood in fecal matter. One of the most successful tests is manufactured and sold by Smith Kline Diagnostics of Sunnyvale, Calif. under the trademark HEMOCCULT and disclosed in Pagano U.S. Pat. No. 3,996,006, which is incorporated herein by reference in its entirety. Briefly, the Pagano test employs an absorbent paper impregnated with a guaiac reagent and encased in a special test slide having openable flaps on both sides of the test slide. To use the Pagano test slide, the physician or a lab technician must obtain a sample of fecal matter, smear it onto the guaiac impregnated paper by opening the panel on one side of the test slide, and thereafter close the panel. A panel on the opposite side of the test slide is then opened and a nonaqueous developing solution is applied to the guaiac impregnated paper. If occult blood is present in the fecal matter smeared on the opposite side of the paper, the guaiac reaction will dye the paper blue, providing a positive indication of the presence of blood in the fecal matter.

Although the Pagano test is effective when used by physicians in their offices and by diagnostic laboratories, it is not the type of test which is readily adaptable for use by the ordinary person. It is cumbersome and requires too many manipulative steps, particularly the step of applying the nonaqueous developing solution to the guaiac impregnated paper.

Schreiber U.S. Pat. No. 5,171,529, which is incorporated herein by reference in its entirety, discloses a device that eliminates the need to have a separate container of developing solution. An absorbent pad holding the developing solution is integrated into the device. After a specimen is placed on one side of the testing paper, the absorbent pad is drawn across the opposing side of the testing paper. While the pad is being drawn across the testing paper, developing solution in the pad is transferred to the testing paper. The testing paper is then observed, for example, visually observed, to determine if a color change has occurred, which indicates the presence of occult blood. However, sufficient and consistent transfer of the developing solution from the absorbent pad to the testing paper is questionable. Further, the used absorbent pad extends from the device disclosed in Schreiber, exposing the user to the developing solution and the contamination on the pad. The developing solution, as with many types of kits, is very reactive and must not be splashed or rubbed on sensitive skin or eyes.

It would be advantageous to provide a system and method, for testing for occult blood, for example, fecal occult blood, that reduces, or even eliminates, the exposure of the user to developing solution that is contaminated with the specimen. Further, it would be advantageous to provide for testing for occult blood that integrates the delivery of the developing solution and the testing paper to reduce system/method complexity and reduce the need for manual dexterity, while providing accurate and reliable results.

SUMMARY OF THE INVENTION

Self-contained systems and methods for testing for the presence of occult blood in a specimen have been discovered. Such systems integrate the developing medium, the delivery of the developing medium, and the testing paper. The present systems eliminate the need for a separate container of developing medium. Such systems also eliminate specimens, for example, fecal matter, splashing onto the system user during and after application of the developing medium in the presence of the specimen.

In one broad aspect of the invention, the present systems comprise a test matrix, a container and a housing. The test matrix includes a testing portion having a specimen placement area on one side and a result area on an opposing second side. In one embodiment, the test portion is offset or spaced apart from a medium entrance portion. The container holds a developing medium and is adapted to release the developing medium onto the test matrix, for example, initially onto the medium entrance portion of the text matrix. The housing holds the test matrix and the container, and includes an opening at the specimen placement area. A result viewing means can be provided for observing the result area. The result viewing means may be an opening in the housing at the result area, or a transparent portion of housing disposed over the result area. The housing preferably further includes a viewing opening located at, that is in line with, the result area of the test matrix. In a more preferred aspect of the invention, a film is disposed across the viewing opening that enables the user to see the result area while inhibiting the developing medium or the fecal sample from escaping through the viewing opening.

Preferably, the container is enclosed by the housing. The container preferably is adapted to release the developing medium upon compression of the container, for example, by applying manual compressive force to the housing. More preferably, the container is adapted to release the developing medium upon breaking the container. In this embodiment a container made of glass is very useful. The housing advantageously comprises a cover for the specimen placement area.

In one embodiment of the invention, the test matrix further comprises a validation area adapted to verify that the system, including the test matrix and the developing medium, is effective, for example, to interact and to indicate the presence of occult blood. The housing preferably comprises a validation viewing means for observing the validation area. The validation viewing means may be an opening in the housing at the validation area or a transparent portion of the housing disposed over the validation area. In a more preferred aspect of the invention, a film, such as a transparent polymeric film, is disposed across the opening that enables the user to see the validation area while inhibiting the developing medium from escaping through the opening.

Preferably, the validation area is closer to the medium entrance portion of the test matrix than is the testing portion. More preferably, a majority of the medium entrance portion is between the testing portion and the validation area of the test matrix.

In one very useful embodiment of the invention, the container holds a free standing liquid developing medium and is positioned and adapted to release the liquid developing medium onto the test matrix. As used herein, the term "free standing liquid" refers to a material which is present as a liquid without being absorbed on an absorbent material. In other words, a "free standing liquid" is a material which preferably is readily visually perceived as being in the liquid phase. The term "free standing liquid" is clearly distinguished from the absorbed developing solution of Schreiber U.S. Pat. No. 5,171,529, noted above.

In another aspect of the present invention, methods for testing for the presence of occult blood in a specimen are provided. Such methods comprise providing a self-contained system including a housing holding a test matrix and a container. The test matrix comprises a testing portion having a specimen placing area on a first side and a result area on a opposing second side. The container holds a developing medium, for example, a free standing liquid developing medium, e.g., developing solution or reagent. The container is adapted to release the developing medium onto the test matrix. The housing includes a specimen opening at the specimen placement area. The present methods further include placing a specimen, for example, of fecal matter, on the specimen placement area; releasing the developing medium from the container onto the test matrix; and observing the result area, for example, the color of the result area, to provide an indication of occult blood in the specimen. The present systems are particularly useful in practicing the present methods.

In a particularly useful embodiment, the present releasing step occurs prior to the placing step. It has been found that releasing the developing medium prior to placing the specimen on the specimen placing area provides for very effective and reliable results. Without wishing to limit the invention to any particular theory of operation, it is believed that releasing the developing medium prior to placing the specimen on the specimen placing area enhances the ability of the developing medium and the test matrix to interact with the specimen in providing an indication of occult blood in the specimen.

Each and every feature and combination of two or more features described herein is included within the scope of the present invention provided that the features included in the combination are not mutually inconsistent.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 2 is a cross-sectional view taken generally along line 2—2 of FIG. 1 with the cover of the system being open and a fecal sample disposed in a specimen opening.

FIG. 3 is a plan view of the housing and cover of the system of FIG. 1 before assembly.

FIG. 5 is a cross-sectional view taken generally along line 2—2 of FIG. 1 with the cover of the system being closed and the container holding developing solution being broken by compression.

FIG. 6 is a plan view of the testing paper used in the system of FIG. 1.

DETAILED DESCRIPTION OF THE DRAWINGS

Figure 1:
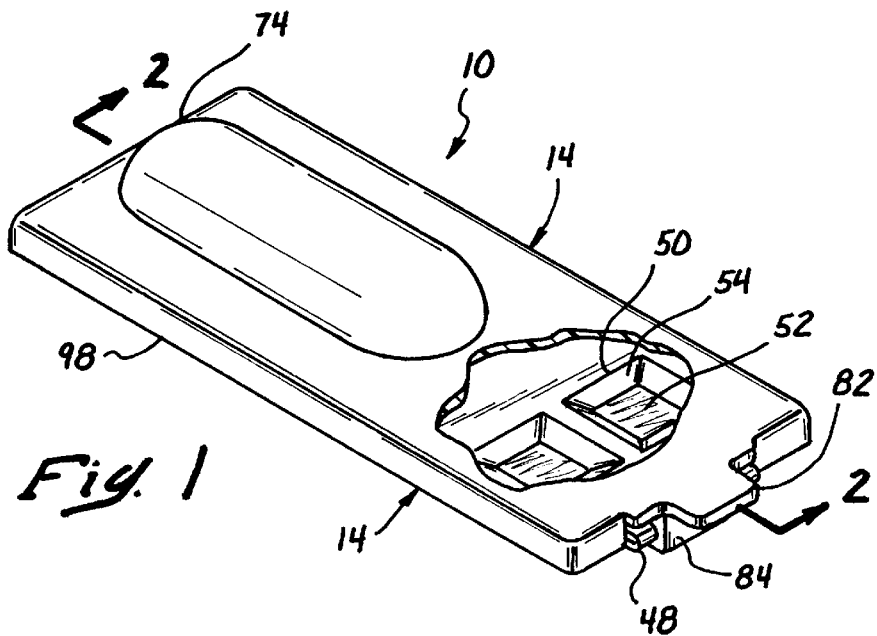
FIG. 1 is a perspective view of an embodiment of a self-contained system for testing fecal occult blood in accordance with the present invention with portions broken away to expose interior details.

Referring now to the drawings, FIGS. 1 and 2 show a self-contained system 10 for testing a specimen 12 of fecal matter for occult blood. The system 10 comprises a housing 14 enclosing a testing paper 16 treated with guaiac and a glass ampule 18 filled with a free standing liquid developing medium, in particular liquid hydrogen peroxide/ethyl alcohol solution 20. The self-contained system 10 enables fecal matter specimens to be tested for occult blood without using an independent developing solution delivery device, such as a eyedropper or pipette (not shown).

Referring now to FIG. 3, the unassembled housing 14 has a bottom section 22 and a top section 24. A cover 26 is joined to the housing 14. The bottom section 22, top section 24 and cover 26 are serially and flexibly joined and are all generally rectangular in shape. The housing 14 and cover 26 are made from a unitary or single piece of plastic or polymeric material, which is a preferred embodiment of the invention. Other embodiments of the invention may include, for example, a housing/cover made of more than one piece, made of materials other than plastic, and/or have sections of other shapes.

Figure 4:
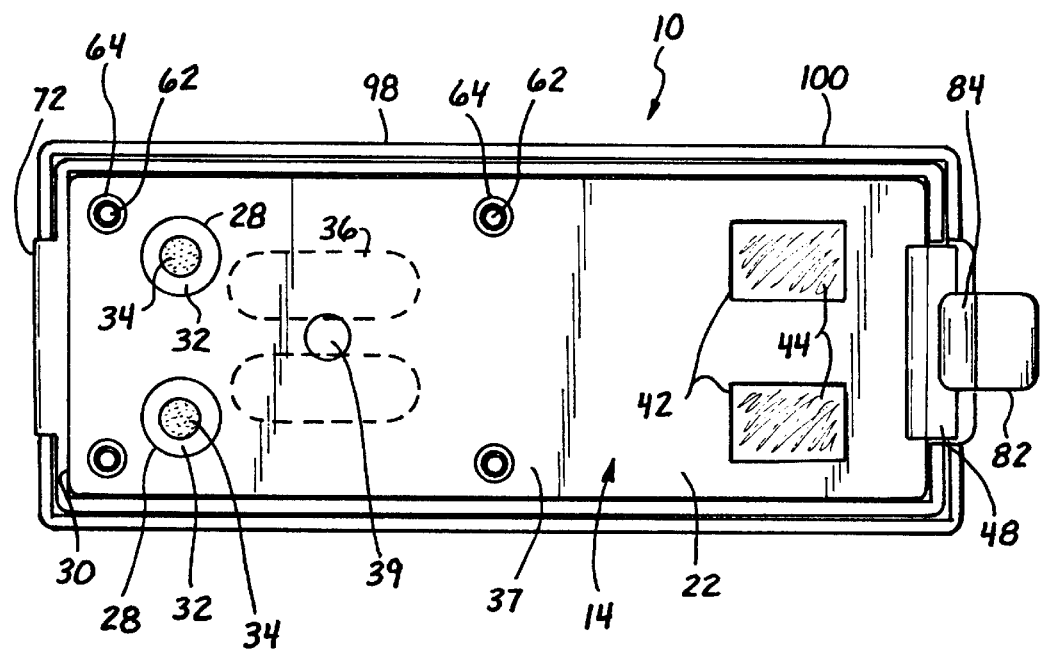
FIG. 4 is a bottom view of the assembled device of FIG. 1.

The bottom section 22 of the housing 14 has two round holes 28 near a first end 30. The round holes have beveled edges 32 for permitting better viewing of validation areas 34 of the testing paper 16, as shown in FIG. 4. Shown to the right of the round holes 28 are two oblong-shaped depressions or depressed areas 36 symmetrically oriented about a major axis 38 of the housing 14. The purpose of the depressions 36 is to decrease rigidity of the bottom section 22 in the general area of the depressions and enable a user of the system 10 to compress and break the ampule 18, as shown in FIG. 5 and described in more detail below. On the bottom surface 37 of the bottom section 22, shown best in FIGS. 4 and 5, is a bump 39 positioned between the depressions 36. Near the second end 40 of the bottom section 22 are two rectangular openings or holes 42 symmetrically oriented about the major axis 38. The rectangular holes 42 expose result areas 44 of the test paper 18.

A first end 46 of the top section 24 is flexibly attached to the second end 40 of the bottom section 22 via a hinge 48. Near the first end 46 are two rectangular openings or holes 50 that are symmetrically oriented about the major axis 38 and align with the rectangular holes 42 of the bottom section 22 when the housing 14 is assembled, as shown in FIGS. 2 and 5. The rectangular holes 50 expose specimen placement areas 52 of the test paper 11, as shown in FIG. 1. The holes 50 have beveled walls 54 to assist in positioning the fecal specimen 12 on the specimen placement area 52. The beveled walls 54 define a recess with enough volume to receive and hold the fecal sample 12 when the cover 26 is closed, as shown in FIG. 5. This aspect is to inhibit excess fecal sample 12 from extruding from the edges of the self-contained system 10 during its use.

An oblong-shaped ampule holding dome 56 extends from a middle section 58 to a second end 60 along the major axis 38. The ampule holding dome 56 is sized to hold the ampule 18. Extending from the dome 56 are two protrusions 59 oriented on the major axis 38. The protrusions 59 facilitate in breaking the ampule 18, as shown in FIG. 5 and discussed in greater detail below.

Disposed about the dome 56 are four small pins 62 that extend through four small holes 64 in the bottom section 22 when the housing 14 is assembled. After extending through the small holes 64, the small pins 62 are heat sealed to fuse the pins in the holes and seal the bottom and top sections, as is shown in FIG. 4. It is advantageous to assemble the housing 14 so that the top section 24 is in close proximity to the bottom section 22. Such assembly holds the test paper 16 tightly between the two sections 22 and 24 of the housing 14 and promotes a wicking action by which developing solution 20 is effectively spread over the test paper. Other embodiments of the invention may use other methods of holding the bottom section 22 and the top section 24 together, such as a series of, for example, four (4), lipped extensions around the periphery of the top section 24 that snap about the periphery of the bottom section 22 upon assembly. The use of such lipped extensions facilitate high speed and efficiency assembly of the present systems.

A first end 70 of the cover 26 is flexibly attached to the second end 60 of the top section 24 via a hinge 72. A dome cover 74 extends from the first end 70 to a middle section 76 of the cover 26. The dome cover 74 covers the ampule dome 56 when the cover 26 disposed on the top section 24, as best shown in FIG. 5. While the ampule dome 56 shape and size is chosen to restrict the movement of the ampule 18 when the system 10 is assembled, embodiments of the invention may have the dome cover 74 of any size and shape that accommodates the dome 56. Extending from the interior surface 75 of the dome 56 are two protrusions 59. The protrusions 59 are aligned with the major axis 38 of the housing, as is best shown in FIG. 3.

At a second end 80 of the cover 26 is a tab 82 extending along the major axis 38 to assist the user of the system 10 in opening and closing the cover. A catch 84 adjacent to the tab 82 engages the hinge 48 when the cover 26 is closed, as best shown in FIGS. 2 and 5. Embodiments of the invention may include any suitable assembly to assist the user in opening and closing the cover 26, and any suitable assembly for securing the cover 26 onto the housing 14.

Referring now to FIG. 6, the test paper 16 shown is generally rectangular in shape with a first end 90 and a second end 92. The two validation areas 34 are disposed near the first end 90. The validation areas 34 comprises a monitor ink that changes color when the ink reacts with the hydrogen peroxide/alcohol solution 20 in the presence of the guaiac in the test paper 16. Different monitor inks are well known in the art, examples of which are disclosed in Lawrence et al. U.S. Pat. No. 4,365,970 and Guadagno et al U.S. Pat. No. 5,196,167 both of which are incorporated herein by reference in their entireties. In the shown embodiment of the invention, the validation areas 34 are round to correspond to the round holes 28 when the system 10 is assembled. Other embodiments of the invention may have other monitor ink patterns, such as a strip of monitor ink extending across the first end 90 of the test paper 16.

A testing portion 93 is located near the second end 92 of the testing paper 16. The testing portion 93 comprises the results areas 44 (shown in dashed lines) on the testing paper surface shown in FIG. 6. On the opposing side of the testing portion 93 are the specimen placement areas 52.

To assemble the self-contained system 10, the liquid filled, glass ampule 18 is placed in the ampule dome 18. Next, the test paper 16 is positioned on an inside surface 94 of the top section 24, the inside surface 94 being shown in FIG. 3. During positioning of the test paper 16, the small pins 62 pierce the paper to assist in holding it in place. The test paper 16 is oriented such that the first end 90 of the paper is disposed at the second end 60 of the top section 24, with the validation areas 34 oriented away from the ampule dome 56. The housing 14 is bent about the hinge 48 such that the bottom section 22 is disposed on the test paper 16 with the small pins 62 extending through the small holes 64. The small pins 62 are then heat fused to the bottom section 22 to seal the top and bottom sections together. At some point during the assembly process, the clip 84 is engaged with the bent hinge 48 to close the cover 26 of the system 10. A lip 96 extends about the periphery of and normal to the inside surface 94. The lip 96 is of the same depth as the thickness of the bottom section 22 such that they are flush after assembly of the system 10. Likewise, a lip 98 extends about the periphery of and down from the cover 26, as best shown in FIG. 2, such that the entire bottom 100 of the device 10 is flush when the cover is closed.

In one embodiment of the invention, a transparent polymer film is disposed between the testing paper 16 and the bottom section 22. The film enables the user to see the testing paper 16 through the two round holes 28 and the two rectangular holes 42 while inhibiting the developing medium 20 or the fecal sample 12 from escaping through the holes. The film may be attached or otherwise sealed to the bottom section 22 such that the developing medium 20 does not migrate around the edges of the film. Alternatively, the film is sealed about the periphery of the holes 28 and 42. The film may be attached to one side of the testing paper 16, or may be crimped in place when the bottom and top sections 22 and 24 are assembled. Other embodiments of the invention may have other suitable approaches to assembling the housing 14 with the film.

A vent may be disposed through the dome 56. The vent enables air to move out of the dome region of the housing during compression of the housing 14. The vent also enables air to flow into the dome region as the developing medium 20 is wicked into the testing paper 16. In a more preferred embodiment, the vent is a plug, for example, of relative dense polymeric material foam, that allows air to move into and out of the dome region, but inhibits liquids from doing the same. In a more preferred embodiment, the plug is hydrophobic so as to inhibit, or even substantially prevent, water or water vapor from getting into the dome region.

To test a fecal specimen 12 for occult blood, the specimen is wiped across or otherwise placed in the rectangular holes 50 so as to contact the specimen placement area 52 of the testing paper 16. The cover 26 is closed onto the top section 24 with the clip 84 engaging the hinge 48, as is shown in FIG. 5. The user compresses the bump 39 to break the glass ampule 18 and release the hydrogen peroxide/alcohol solution 20. The bump 39 is to assist in locating an optimum place to compress the bottom section 22. During compression and breakage of the ampule, the two protrusions 59 contact the ampule 18, and focus the breaking compression load on the ampule at the protrusion contact spots 79. As the breaking compression load is focused, the ampule 18 also breaks at the contact spots 79 with relative ease. Other embodiments of the invention may have other assemblies for assisting the user to release the solution 20. Other compression assisting assemblies may include, for example, a weakening in the housing 14 other than by a thinning the bottom section 22 through the depressions 36, and other types of devices for focusing the breaking compression load.

After compression and breakage of the ampule 18, the hydrogen peroxide/alcohol solution 20 initially enters into the testing paper 16 at a solution entrance portion 102. The solution entrance portion 102 corresponds to the region of the testing paper 16 under the dome 56, as shown in FIGS. 2 and 5. From the solution entrance portion 102, the solution 20 migrates, for example, by wicking action, to the validation areas 34 and the testing portion 93.

After the solution 20 migrates to the testing portion 93, the solution 20 interacts with the specimen 12 on the specimen placement area 52 to turn blue if occult blood is present in the specimen. The appearance of blue is observed at the result area 44 corresponding to the specimen placement area 52. The color change occurs as a result of a number of interactions. One reaction is that the alcohol in the solution 20 dissolves the guaiac in the testing paper 16. Another reaction is that a portion of the specimen 12 is dissolved into the solution 20. In another reaction, any blood present in the dissolved portion of the specimen 12 reacts with the hydrogen peroxide of the solution 20 to release oxygen. In another reaction, the released oxygen interacts with the dissolved guaiac to change the color of the guaiac to blue.

In one embodiment, the developing solution 20 is released from the ampule 18 before the specimen 12 is placed on the specimen placement area 52. This embodiment has been found to provide very reliable indications of the presence/absence of occult blood in the specimen 12.

Due to the inherent properties of hydrogen peroxide, the solution may not be potent enough to provide oxygen and, thereby, initiate a color change in the guaiac in the presence of blood. To determine if the solution is sufficiently potent, and in general to determine if system 10 is effective to indicate the presence of occult blood, the user observes the color of the validation areas 34. More specifically, if the solution is potent and/or system 10 is effective as an occult blood indicator, the monitor ink at the validation areas 34 with change color to blue. Embodiments of the system 10 may take many forms. For example, there may be more or less holes 28 exposing more or less validation areas; there may be more or less result areas 44 and specimen areas 54 with corresponding holes 42 and 50. Further, the holes 42 and 50 and the areas 44 and 54 may be of other shapes.

In the shown embodiment of the invention, the testing portion 93 of the testing paper 16 is offset or spaced apart from the validation areas 34. Further, the validation areas 34 overlap the solution entrance portion 102 and are closer to the solution entrance portion than is the testing portion 93. Also, the solution entrance portion 102 is located between the validation areas 34 and the testing portion 93. The positioning of the solution entrance portion 102, the validation areas 34, and the testing portion 93 is to inhibit cross contamination of the monitor ink or the blood, which could invalidate the test. Other embodiments of the invention may have other arrangements of the validation areas 34 and testing portion 93 of the testing paper 16. Still further embodiments of the invention may have channels or other features in the housing 14 which are effective in directing the solution 20 to the validation areas 34 and the testing portion 93.

The shown, and preferred, embodiment of the invention has four small pins 62/small holes 64 for sealing the bottom section 22 to the top section 24 to snugly dispose the testing paper 16 between the bottom section 22 and the top section 24. If the testing paper 16 is not snugly fit, voids in the top section 24/testing paper 16/bottom section 22 arrangement may collect the solution 20 and inhibit transfer thereof to the testing portion 93. Other embodiments of the invention may have more or less small pins/small holes arrangements or other assemblies for sealing the top section 24 to the bottom section 22.

Other embodiments of the invention may have other means for viewing the validation areas 34 and the results areas 44, such as a transparent plastic insert in the holes 28 and 42 or having a bottom section 22 that is entirely transparent. Other embodiments of the invention may not have a cover 26, or may have a partial cover. Still further embodiments of the invention may have a bottom cover or label (not shown) that covers the bottom surface 37 of the bottom section 22 to inhibit contamination or mutilation of the validation areas 32 and the results areas 44.

Containers of solution 20 other than the glass ampule 18 of the shown and preferred embodiment may be employed. For example, another type of container that is enclosed by the housing, or held by the housing may be used. The solution container preferably is adapted to release the solution onto a solution entrance portion 102 of the testing paper 16. Such containers may break or otherwise open upon compression, as with the glass ampule 18. Other embodiments of the invention may include a member that is pulled, thereby breaking or otherwise opening the container.

Embodiments of the invention may comprise containers that are compressed to force the developing solution through an opening, such as a flexible bladder or a plunger/cylinder arrangement. The container in these embodiments may be enclosed by the housing 14, as is shown in the drawings. The container may be external and integrated with the housing. In embodiments with the container being integrated yet external to the housing, it is noted that the internal volume of the assembled housing is equal to or greater than the amount of developing medium in the container to reduce the incidence of developing medium flowing from the housing during compression of the container.

Any suitable insoluble, for example, water and/or ethyl alcohol insoluble, matrix in place of the testing paper 16. Any suitable oxygen donor, such as cumene hydroperoxide, other peroxides and the like, may be used in place of the hydrogen peroxide in the solution. Embodiments of the invention may use any suitable chromogen in place of the guaiac, such as leuco dyes including tetramethyl benzidine and ortho toluidine, cresol, catechol, 3,3',5,5'-tetramethylbenzidine, p-toluidine, betanaphthol, pyrogallol, o-phenylenediamine, leuco malachite green, 3-amino ethylcarbazole, 4-amino antipyrine, phenol, 2,2'-azino-di-(3-ethylbenzyl)azoline sulfonic acid (ABTS), and mixtures thereof, as is disclosed in Lawrence U.S. Pat. No. 4,939,097, which is incorporated herein by reference in its entirety. The test matrix may be coated to prevent oxidation of the chromogen, as is disclosed in Detweiler et al. U.S. Pat. No. 4,382,064, which is incorporated herein by reference in its entirety.

Embodiments of the invention may have enhanced sensitivity and specificity characteristics. To reduce the incidence of false positive results from the presence of plant peroxidases in the specimen, a peroxidase denaturing agent, such as urea, guanidine hydrochloride and the like, together with a metal chelating agent to sequester calcium and magnesium ions that are essential to the peroxidase activity may be used, as disclosed in Fleisher U.S. Pat. No. 4,333,734, which is incorporated herein by reference in its entirety. Polar solvents, such as dimethyl sulfoxide, dimethyl formamide and the like, which stabilize the hydroperoxide and the leuco dye may be employed, as disclosed in Lam U.S. Pat. No. 4,071,317, which is incorporated herein by reference in its entirety. Embodiments of the invention may also employ (1) a developing and complete reagent solution that uses as a solvent system, a solvent including at least about 50% by volume, a solvent for iron protoporphyrins, such as dimethyl sulfoxide and the like, and/or (2) a multi-chromogen comprised of a mixture of guaiac and ABTS. The system may incorporate hemoprotein solubilizing agents, plant peroxidase inhibitors, meat peroxide inhibitors, iron/copper chelating agents, accelerators, buffers and like in the developing medium or solution. Examples are disclosed in Lawrence U.S. Pat. Nos. 4,818,702, 4,937,197, and 4,939,097, each of which is incorporated herein by reference in its entirety.

Embodiments of the invention may employ enhancers to produce a more intense, and readable, indication or endpoint. Examples of such enhancers include phenolic type compounds, such as esters of hydroxybenzoic acid, parabens, phenol, guaiacol, p-hydroxybenzoic acid, 3,5-dimethylphenol, methyl salicylate, 3-5, dichlorophenol, p-nitrophenol, p-bromophenol and the like. One or more of these enhancers may be present in an amount in the range of about 0.4% to about 20% by weight in the developing solution 20, as disclosed in Baker et al U.S. Pat. Nos. 5,310,680 and 5,391,498, each of which is incorporated herein by reference in its entirety.

While this invention has been described with respect to various specific examples and embodiments, it is to be understood that the invention is not limited thereto and that it can be variously practiced within the scope of the following claims.

What is claimed is:

1. A self-contained system for testing for the presence of occult blood in a specimen, the system comprising:
   a test matrix extending along a major axis, the test matrix comprising a thickness, the thickness extending substantially perpendicular to the major axis and including a testing portion spaced apart from a developing medium entrance portion, the testing portion comprising a specimen placement area on a first side of the thickness and a result area on an opposing second side directly across the thickness from the result area;
   a container holding a developing medium, wherein the container is adapted to release the developing medium onto initially the developing medium entrance portion; and
   a housing holding the test matrix and the container, the housing including an opening located at the specimen placement area and a cover structured and positioned to cooperate with the housing and the specimen placement area to define an enclosure for confining and maintaining a specimen on the specimen placement area with the cover positively closed over the specimen.

2. The system of claim 1, wherein the housing is structured so than the cover is openable to allow a substantially solid specimen to be placed on the specimen placement area and includes a latch for securing the cover in a positively closed position over a specimen located on the specimen placement area.

3. The system of claim 1, wherein the container is enclosed by the housing.

4. The system of claim 1, wherein the housing further comprises a result viewing opening located at the result area.

5. The system of claim 1, wherein the container is adapted to release the developing medium upon breaking the container.

6. The system of claim 5, wherein the container comprises glass.

7. A self-contained system for testing for the presence of occult blood in a specimen, the system comprising:
   a test matrix extending along a major axis, the test matrix having a thickness extending substantially perpendicular to the major axis and including a testing portion having a specimen placement area on a first side of the thickness and a result area on an opposing second side directly across the thickness from the result area;
   a container holding a free standing liquid developing medium, wherein the container is positioned and adapted to release the liquid developing medium onto the test matrix; and
   a housing holding the test matrix and the container, the housing including a specimen opening located at the specimen placement area and a cover structured and positioned to cooperate with the housing and the specimen placement area to define an enclosure for confining and maintaining a specimen on the specimen placement area with the cover positively closed over the specimen.

8. The system of claim 7, wherein the housing is structured so that the cover is openable to allow a substantially solid specimen to be placed on the specimen placement area and includes a latch for securing the cover in a positively closed position over a specimen located on the specimen placement area.

9. The, system of claim 7, wherein the container is enclosed by the housing.

10. The system of claim 7, wherein the container is adapted to release the developing medium upon compression of the container.

11. The system of claim 7, wherein:
   the container is enclosed by the housing;
   the container is adapted to release the liquid developing medium upon compression of the container; and
   the housing is adapted to enable the container to be compressed.

12. A self-contained system for testing for the presence of occult blood in a specimen, the system comprising:
   a test matrix consisting essentially of a thickness, a testing portion having a specimen placement area on a first side. and a result area on an opposing second side, and a validation area spaced apart from the testing portion with only a portion of the testing matrix between the testing portion and the validation area;
   a container holding a developing medium, wherein the container is adapted to release the developing medium onto the test matrix upon compression of the container; and
   a housing having a major axis, and holding the test matrix and the container, and including an opening at the specimen placement area and a result viewing opening located at the result area, the thickness of the test matrix extending substantially perpendicular to the major axis and the result area being located directly across the thickness of the test matrix from the specimen. placement area;
   wherein the validation area is positioned to verify than the developing medium and test matrix are effective to indicate the presence of occult blood.

13. The system of claim 12, wherein the container is enclosed by the housing.

14. The system of claim 12, wherein the container is adapted to release the developing medium upon breaking the container.

15. The system of claim 12, wherein the container comprises glass.

16. The system of claim 12, wherein:
the container is enclosed by the housing;
the container is adapted to release the developing medium upon compression of the container; and
the housing is adapted to enable the container to be compressed.

17. The system of claim 12, which further comprises a fecal matter specimen located on the specimen placement area.

18. The system of claim 12, herein the housing further includes a cover structured and positioned to be opened to allot a specimen to be placed on the specimen placement area and to be, positively closed and maintained closed to cover a specimen located on the specimen placement area.

19. The system of claim 12, wherein the validation area is closer to the medium entrance portion than is the testing portion.

20. The system of claim 12, wherein the validation area is near a first end of the test matrix and the testing portion is near an opposing second end of the test matrix, and wherein the container is located between the validation area and the testing portion, such that the validation area and testing portion are in opposite flow directions relative the container.

21. The system of claim 12, wherein the housing is unitary.

22. A method for testing for the presence of occult blood in a specimen, the method comprising:

providing a self-contained system comprising a housing having a major axis and holding a test matrix and a container adapted to release a free-standing developing medium on the test matrix, wherein the test matrix comprises a thickness substantially perpendicular to the major axis, a testing portion having a specimen placement area on a first side and a result area on an opposing second side directly across the thickness of the test matrix from the specimen placement area, the housing includes an opening located at the specimen placement area and a cover having an open position and a closed position, wherein the cover is structured and positioned relative the housing to allow placement of a specimen on the specimen placement area when in the open position and to cooperate with the housing and the specimen placement area to define an enclosure for confining and maintaining a specimen on the specimen placement area when in the closed position;

placing the specimen on the specimen placement area thereafter;

positively closing the cover to maintain the specimen on the specimen placement area;

thereafter releasing the developing medium from the container onto the test matrix; and observing the result area.

23. The method of claim 22, wherein the releasing step comprises compressing the container.

24. The method of claim 22, wherein the releasing step comprises breaking the container.

* * * * *